United States Patent [19]

Fanning et al.

[11] Patent Number: 5,051,497

[45] Date of Patent: Sep. 24, 1991

[54] METHOD FOR THE SOLUBILIZATION OF AN OTHERWISE INSOLUBLE PROTEIN

[75] Inventors: Ellen Fanning, Munich; Adolf Höss, Hausham; Avril Arthur, Munich, all of Fed. Rep. of Germany

[73] Assignee: Consortium fur elektrochemische Industrie GmbH, Munich, Fed. Rep. of Germany

[21] Appl. No.: 298,683

[22] Filed: Jan. 19, 1989

[30] Foreign Application Priority Data

Jan. 25, 1988 [DE] Fed. Rep. of Germany ....... 3802045
Sep. 27, 1988 [EP] European Pat. Off. .......... 88115908

[51] Int. Cl.$^5$ ................................. C07K 3/22
[52] U.S. Cl. .................................. 530/416; 530/417; 530/399; 530/412; 435/69.1; 435/69.52
[58] Field of Search ............... 435/68, 69.1, 69.52; 530/416, 417, 399, 350, 412

[56] References Cited

U.S. PATENT DOCUMENTS 4,757,013 7/1988 Inouye et al. ............... 435/172.3
4,766,224 8/1988 Rausch ......................... 530/412

FOREIGN PATENT DOCUMENTS 0114506 8/1984 European Pat. Off. .

OTHER PUBLICATIONS

Hoess et al., 1988, Bio/Technology 6:1214–1217.
Malm, B., 1987, J. Immunol. Meth. 104:103–109.
Sharma, S. K., 1986, Separation Science and Technology 21(8):701–726.
Biochem, J. (1986) 240, 1–12 (Printed in Great Britain), Review article, "The Purification of Eukaryotic Polypeptides Synthesized in *Escherichia Coli*", Fiona A. O. Marston.
Proc. Natl. Acad. Sci. U.S.A., vol. 84, pp. 5700–5704, Aug. 1987, Biochemistry, "Drosophila Kruppel Gene Product Produced in a Baculovirus Expression System is a Nuclear Phosphoprotin that Binds to DNA", Roger Ollo & Tom Maniatis.
"Cytoplasmic Inclusion Bodies in *Escherichia coli* Producing Biosynthetic Human Insulin Proteins", E. Vol. 215, Feb. 1982.
European Journal of Cell Biology 31, 171–174 (1983), "Immunocytochemical Demonstration of Human Proinsulin Chimeric Polypeptide within Cytoplasmic Inclusion Bodies of *Escherichia coli*", Donald C. Paul et al.
Protein Purification: Micro t Macro, pp. 429–442, "Solubilisation, Refolding and Purification of Eukaryotic Proteins Expressed in *E. coli*", Peter E. Lower, et al.
"The Purification of Eukaryotic Polypeptides Expressed in *Escherichia coli*", Fiona A. O. Marston.
Journal of Virology, Jun. 1988, p. 1999–2006, vol. 62, No. 6, copyright 1988, American Society for Microbiology "Expression of Simian Virus 40 T Antigen in *Escherichia coli*: Localization of T-Antigen Origin DNA-- Binding Domain to Within 129 Amino Acids", Avril K. Arthur, et al.
"Molecular Mechanism of Action of the Antiobiotic Rifampicin", by Guido R. Hartmann, et al.
The Journal of Immunology copyright 1978 by The Williams & Wilkins Co., vol. 120, No. 6, Jun. 1978, "T Cell Growth Factor: Parameters of Production and a Quantitative Microassay for Activity", Steven Gillis, et al.
Vol. 9, No. 2, 1981, Nucleic Acids Research, "A System for Shotgun DNA Sequencing", Joachim Messing et al.
J. Mol. Biol. (1969) 41, 459–472, "A Complementation Analysis of the Restriction and Modification of DNA in *Escherichia coli*", Herbert W. Boyer and Daisy Roulland-Dussoix.

(List continued on next page.)

Primary Examiner—Margaret Moskowitz
Assistant Examiner—Keith L. Furman
Attorney, Agent, or Firm—Collard, Roe & Galgano

[57] ABSTRACT

The invention relates to a method for the solubilization, by means of ion exchanger resins, of otherwise insoluble protein expressed by cultivated cells.

10 Claims, 1 Drawing Sheet

OTHER PUBLICATIONS

Proc. Natl. Acad. Sci. U.S.A., vol. 81, pp. 6647–6651, Nov. 1984, Biochemistry, "Heat Shock Regulatory Gene htpR Influences Rates of Protein Degradation and Expression of the Lon Gene in *Escherichia coli*", Stephen A. Goff et al.

The EMBO Journal, vol. 6, No. 9, pp. 2719–2725, 1987, "The Highly Conserved Amino-Terminal Region of the Protein Ended by the V-Myb Oncogene Functions as a DNA-Binding Domain", Karl-Heinz Klempnauer and Albert E. Sippel.

Journal of Virology, Sep. 1981, pp. 861–869, vol. 39, No. 3, "Monoclonal Antibodies Specific for Simian Virus 40 Tumor Antigens", Ed Harlow et al.

Biochemistry 1983, 22, 251–255, "Neutral Glycosphinogolipids of Murine Myeloma Cells and Helper, Cytolytic, and Suppressor T Lymphocytes", Bernhard Kniep et al.

Journal of Virology, Jul. 1987, pp. 2076–2083, vol. 61, No. 7, copyright 1987, American Society for Microbiology, "Oligomerization and Origin DNA-Binding Activity of Simian Virus 40 Large T Antigen", Robert Runzler et al.

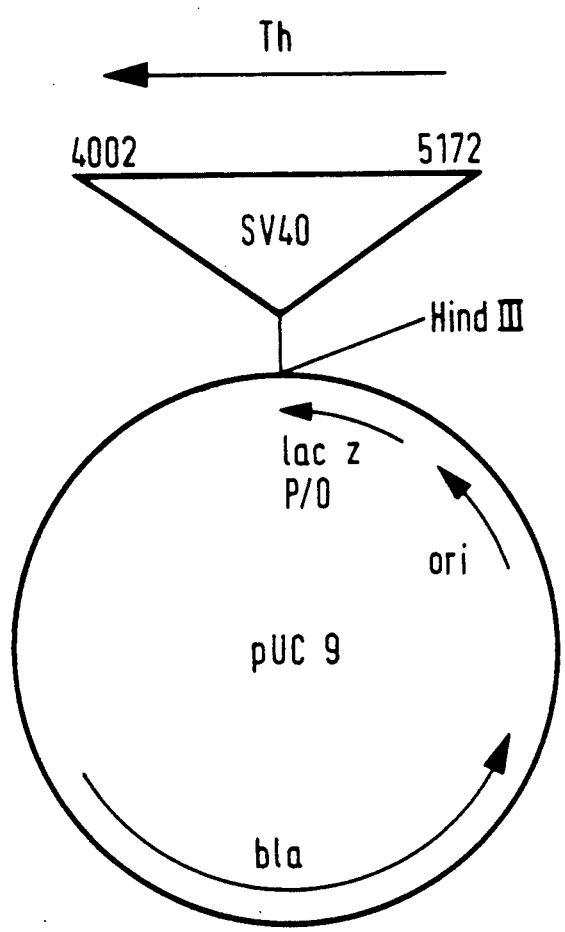

METHOD FOR THE SOLUBILIZATION OF AN OTHERWISE INSOLUBLE PROTEIN

BACKGROUND OF THE INVENTION

1. Field of the Invention

The present invention relates to a method for the solubilization of an otherwise insoluble protein expressed by cultivated cells.

Cultivated cells, especially bacteria, in particular *Escherichia coli*, are used industrially for the overproduction of proteins, especially of proteins which are encoded by cloned genes of other organisms. Satisfactory overexpression of proteins of commercial interest has succeeded in many cases, as demonstrated by the examples of interferon-$\beta$ and insulin. However, it has emerged that there may be problems with the overproduction as a result of the insolubility of overexpressed proteins. A review on *E. coli* is to be found in *Biotechnology*, 5 (1987) 883–890.

2. The Prior Art

The proteins are deposited as inclusion bodies which are visible under the electron microscope; cf., for example, *Science*, 215 (1982) 687–689. While these inclusion bodies have the advantage that the recombinant proteins are substantially protected from proteolysis; cf., for example, *EMBO Journal*, 3 (1984) 1429–1434, the isolation of recombinant proteins in solubilized or active form from these inclusion bodies or deposits is associated with great difficulties. Often urea, sodium dodecyl sulfate (SDS) or other denaturing agents are used to dissolve the proteins. These detergents, however, lead to an undesired denaturation of the proteins; cf., for example, the following reviews: *Marston* (1987), the purification of eukaryotic polypeptides expressed in *Escherichia coli*. In *DNA Cloning*, Vol. III, ed. D. Glover, pages 59–88, IRL Press, Oxford; *PNAS*, 80 (1983) 906–910 or *PNAS*, 82 (1985) 2354–2358. However, a renaturation is associated with losses of active material, in particular, as the renaturation is not, as a rule, complete. There are also cases in which the renaturation is no longer possible, so that it is necessary to forego the insoluble protein, and use only the soluble fraction as a source of protein cf., for example, *Biotechnology*, 5 (1987), 960–965.

SUMMARY OF THE INVENTION

The goal of solubilizing otherwise insoluble proteins, which have been expressed by cultivated cells, has now been achieved, according to the present invention, by a method in which the insoluble protein is contacted with an ion exchanger and then again separated from it.

The main advantage of the procedure, according to the invention, is that it is possible to dispense with denaturing agents or detergents. Moreover, the method, according to the invention, can be carried out easily and readily, and a virtually quantitative yield of solubilized protein results can be obtained.

Although it is known how to adsorb proteins after removal of insoluble material, by centrifugation, onto ion exchangers, only soluble proteins have been employed in this known method—which is not surprising; cf., for example, *Current Protocols in Molecular Biology*, 1987, page 10.9.2, New York (Greene Publ. Assoc. and Wiley-Interscience). This state of the art is of importance to the extent that the person with ordinary biochemical skills is familiar with the choice of suitable ion exchangers when a particular protein is employed.

It is possible to apply the method, according to the invention, to proteins expressed by bacteria cultivated industrially, such as *E. coli*, in particular. The method according to the invention, can, however, also be applied to proteins expressed by eukaryotic cells maintained industrially in tissue cultures, such as, for example, insect cells; cf., for example, *PNAS*, 84 (1987) 5700–5804 or *Genetic Engineering*, 8 (1986) 277–298.

When carrying out the method according to the invention, it is possible to contact the insoluble protein with an ion exchanger in the culture broth in the presence of the disrupted cells, and of the cell debris. Of course, it is also possible for the insoluble protein to be contacted with an ion exchanger after prior removal of the disrupted cells, and of the cell debris.

Given the simplicity of the claimed method, routine suitability tests may be expected of the biochemist of ordinary skill in order to choose a suitable ion exchanger for a particular protein. Furthermore, the aforementioned state of the art will help to provide guidance for the skilled laboratory scientist.

The matrix of the ion exchanger may be organic in nature or an organic polymer or a polysaccharide, for example, agarose. Examples of ion exchangers which can be employed according to the invention are Sepharoses. A specific example of an ion exchanger which can be employed not merely for the solubilization of a single specific protein is Q-SEPHAROSE (Q-SEPHAROSE Fast-Flow from Pharmacia; Freiburg, Federal Republic of Germany). Q-SEPHAROSE is an example of an anion exchanger. Anion exchangers of this type will be used in a basic medium. However, it is also possible to use cation exchangers when an acid medium is provided; for example, S-Sepharose (S-Sepharox Fast-Flow from Pharmacia) may also be used.

Q-SEPHAROSE FAST FLOW is a strong anion exchanger. The gel is made of 6% cross-linked agarose matrix. The ion exchange group and the short spacer arm that attaches the group to the agarose matrix is $—CH_2—N^+(CH_3)_3$, the counter ion is $SO_4^{2-}$.

S-SEPHAROSE FAST FLOW is a strong cation exchanger. The gel is made of 6% cross-linked agarose matrix. The ion exchange group and the short spacer arm that attaches the group to the agarose matrix is $—CH_2—SO_3—$. The counter ion is $Na^+$.

SORVALL SS34 is a superspeed fixed angle rotor centrifuge.

If, for example, bacterial cells are used for the overproduction of a particular protein, it is possible for the cells to be disrupted in a known manner, for example by ultrasound, lysozyme, osmotic shock, freezing/thawing, or a combination of these measures. To protect the protein, the liquid medium is preferably buffered. It is advantageous, in larger scale processes, to add the ion exchanger material to the buffered culture medium without removing the disrupted cells and the cell debris. If the ion exchanger material is added in the form of granules, it can be removed from the culture medium after a given time, e.g., after 1 to 2 hrs., by filtration or centrifugation. Optionally, the adsorbed protein is then eluted from the ion exchanger, for example, by addition of a salt-containing buffer. The removal of the ion exchanger from the protein-containing liquid medium can, in turn, be carried out by filtration or centrifugation. The protein-containing liquid medium can be worked up in a known manner in order to obtain or utilize the protein.

DETAILED DESCRIPTION OF THE DRAWING

The invention will now be explained using the following examples and the accompanying drawing which is a circular plasmid map of path (c.f., *J. Virol.*, 62 (1988) 1999-2006.

EXAMPLE 1

Solubilization of the SV40-T antigen derivate Th (peptide Th).

5 ml of *E. coli* cells (JM 103, cf. *Nucleic Acids Res.*, 9 (1981) 309-321, which contained the plasmid pTh (see FIG.) and had been cultivated overnight, were induced with 5 mM isopropyl-$\beta$-D-thiogalactopyranoside (IPTG) in 100 ml of L-broth medium at 37° C. for 4 hrs. The mixture was then centrifuged at 8000 rpm in a centrifuge (SORVALL SS34 Rotor) for 5 min. The supernatant, the L-broth medium, was poured off, and the pellet was resuspended in 2.5 ml of buffer A [buffer A: 50 mM Tris-HCL (pH 8.0), 50 mM NaCl, 1 mM EDTA (ethylenediaminetetra acetic acid), 1 mM DTT (dithiothreitol), 1 mM PMSF (phenylmethylsulfonylflouride), and 10% glycerol]. In order to disrupt the cells, lysozyme (5 mg/ml) was added to the suspension, and the suspension was kept on ice for 15 min., sonicated 3×20 sec. with ultrasound and again placed on ice for 15 min. The lysate was added to the same volume of Q-Sepharose Fast-Flow (Q-SEPHAROSE FF) equilibrated in buffer A. The system was then shaken on a rotator at 4° C. for 2 hrs. and was then centrifuged at 5000 rpm for 15 min. The supernatant was discarded. The precipitate was taken up in the same volume of buffer B (buffer B: buffer A but with NaCl concentration 250 mM). The mixture was then shaken on a rotator at 4° C. for 15 min. and finally centrifuged at 5000 rpm for 15 min. The supernatant was employed to determine the Th activity in a DNA-binding assay. The results are shown in Table 1.

TABLE 1

DNA-binding assay of Th (isolation as in Example 1)

| Fraction | Volume (ul) | Densitometer measurement (%) | Th conc. (ug) | DNA-binding activity (%) |
|---|---|---|---|---|
| Total Lysate | 500 | 5.6 | 2 | 100 |
| Supernatant from binding to Q-SEPHAROSE | 500 | 0.0 | 0 | 0 |
| Eluate of the Lysate from Q-SEPHAROSE | 500 | 16.7 | 6 | 298 |

EXAMPLE 2

Solubilization of SV40-T-antigen (Th)

Example 1 was repeated with the exception that, after disruption of the cells, centrifugation at 4° C. was carried out for 15 min. and the supernatant, on the one hand, and the precipitate resuspended in buffer A, on the other hand, were treated with the ion exchanger. The activity of the renatured protein was confirmed as in Example 1 (Table 2).

TABLE 2

DNA-binding assay of Th (isolation as in Example 2)

| Fraction | Volume (ul) | Densitometer measurement (%) | Th conc. (ug) | DNA-binding activity (%) |
|---|---|---|---|---|
| Total Lysate | 500 | 5.6 | 2 | 100 |
| Eluate of the supernatant from Q-SEPHAROSE | 500 | 5.8 | 2 | 99 |
| Eluate of the pellet from Q-SEPHAROSE | 500 | 10.9 | 4 | 194 |

EXAMPLE 3

Solubilization of Interleukin-2 (IL-2)

Example 1 was repeated with the difference that, in place of SV40-T-antigen, solubilization this time was of IL-2 which had been produced by *E.-coli* cells which contained the plasmid ptac4 (cf., Hoechst AG, Frankfurt, Federal Republic of Germany).

The NaCl concentration in buffer B differed from that in Example 1, being increased to 500 mM NaCl. The activity of the solubilized IL-2 was confirmed by a T-cell growth assay (see Table 3).

TABLE 3

Activity assay for IL-2 using CL3 T-cells (isolation of the IL-2 as in Example 3)

| Fraction | Thymidine incorporation (cpm)* | IL-2 activity (%) |
|---|---|---|
| Total Lysate | 2617.0 | 100 |
| Supernatant from binding to Q-SEPHAROSE FF | 178 | 7 |
| Eluate of the Lysate from Q-SEPHAROSE FF | 5379.5 | 205 |

*counts per minute

EXAMPLE 4

Solubilization of Interleukin-2 (IL-2)

Example 3 was repeated with the exception that, after disruption of the cells, centrifugation at 4° C. was carried out for 15 min., and the supernatant, on the one hand, and the precipitate resuspended in buffer A, on the other hand, were treated with the ion exchanger. The activity of the solubilized protein was confirmed as in Example 3 (see Table 4).

TABLE 4

Activity assay for IL-2 using CL3 T-cells** (isolation of the IL-2 as in Example 4)

| Fraction | Thymidine incorporation (cpm)* | IL-2 activity (%) |
|---|---|---|
| Total Lysate | 2617.0 | 100 |
| Eluate of the supernatant from Q-SEPHAROSE FF | 2583.0 | 99 |
| Eluate of the pellet from Q-SEPHAROSE FF | 2808.5 | 107 |

*cpm = counts per minute
**(cf. Biochemistry, 22 (1983) 251-255)

EXAMPLE 5:

Solubilization of v-myb

Inclusion bodies of the retroviral oncoprotein v-myb, which had been produced by *E. coli* HB101, cf. *J. Mol. Biol.*, 41, (with trp-control [trp—cf. customary commercially available promoter]; pVM2028, cf. EMBO J., 6 (1987) 2719–2725), could be solubilized with S-SEPHAROSE Fast-Flow (S-Sepharose FF); and adsorption to the cation exchanger could not be observed.

EXAMPLE 6

Solubilization of T260*

In an analogous manner to Example 5, inclusion bodies of the T-antigen peptide T260 could be solubilized with S-SEPHAROSE.

*cf. J. Virol. 62 (1988) 1999–2006

EXAMPLES 7 AND 8

Solubilization of 3d$^{rif}$*

In an analogous manner to Example 1, inclusion bodies of a bacterial membrane protein, which is responsible for a Rifampicin resistance of a new type, could be solubilized with Q-SEPHAROSE and phenyl-Sepharose as well.

*cf. P. Heinrich (1987) Doctoral thesis, University of Munich.

While only several examples of the present invention have been described, it will be obvious to those of ordinary skill in the art, that many modifications may be made thereto without detracting from the spirit and scope thereof.

What is claimed is:

1. A process for the solubilization of a protein comprising the steps of:
   contacting an insoluble protein expressed by cultivated cells in the form of inclusion bodies with an ion exchanger; and
   separating said protein from the ion exchanger in a solubilized form whereby in the steps of contacting and separating the use of denaturing agents and detergents is excluded.

2. The process according to claim 1, wherein in said contacting step, said protein being in a culture broth is contacted with the ion exchanger in the presence of disrupted cells and of a cell debris.

3. The process according to claim 1, further comprising the step of removing disrupted cells and cell debris prior to said contacting step wherein said protein is contacted with the ion exchanger.

4. The process according to claim 1, wherein said ion exchanger is in the form of granules.

5. The process according to claim 1, wherein said ion exchanger is an anion exchanger.

6. The process according to claim 5, wherein said anion exchanger is Q-SEPHAROSE which comprises
   a gel made of 6% cross-linked agarose matrix;
   an ion exchange group and a short spacer arm that attaches the group to the agarose matrix being —$CH_2$—$N^+(CH_3)_3$; and
   a counter ion being $SO_4^{2-}$.

7. The process according to claim 1, wherein said ion exchanger is a cation exchanger.

8. The process according to claim 7, wherein said cation exchanger is S-SEPHAROSE which comprises
   a gel made of 6% cross-linked agarose matrix;
   an ion exchange group and a short spacer arm that attaches the group to the agarose matrix —$CH_2$—$SO_3$—; and
   a counter ion being $Na^+$.

9. The process according to claim 1, wherein said separating step is carried out by eluting.

10. The process according to claim 1, wherein a protein expressed by *Escherichia coli* is solubilized.

* * * * *